United States Patent
Guo et al.

(10) Patent No.: US 11,172,934 B2
(45) Date of Patent: Nov. 16, 2021

(54) EMBOLISM COIL CONVEYING DEVICE AND PREPARATION METHOD THEREFOR

(71) Applicant: MICROPORT NEUROTECH (SHANGHAI) CO., LTD., Shanghai (CN)

(72) Inventors: Yuanyi Guo, Shanghai (CN); Yunfei Peng, Shanghai (CN); Bing Chen, Shanghai (CN); Mengqi Chang, Shanghai (CN); Hairui Yu, Shanghai (CN); Qiaorong Jin, Shanghai (CN); Yiqun Bruce Wang, Shanghai (CN); Zhiyong Xie, Shanghai (CN)

(73) Assignee: MICROPORT NEUROTECH (SHANGHAI) CO., LTD., Shanghai (CN)

( * ) Notice: Subject to any disclaimer, the term of this patent is extended or adjusted under 35 U.S.C. 154(b) by 26 days.

(21) Appl. No.: 16/639,456

(22) PCT Filed: Aug. 9, 2018

(86) PCT No.: PCT/CN2018/099541
§ 371 (c)(1),
(2) Date: Feb. 14, 2020

(87) PCT Pub. No.: WO2019/033978
PCT Pub. Date: Feb. 21, 2019

(65) Prior Publication Data
US 2020/0281598 A1    Sep. 10, 2020

(30) Foreign Application Priority Data

Aug. 16, 2017    (CN) .......................... 201710703690.0

(51) Int. Cl.
*A61B 17/12*    (2006.01)
*A61B 17/00*    (2006.01)

(52) U.S. Cl.
CPC .... *A61B 17/1214* (2013.01); *A61B 17/12113* (2013.01); *A61B 2017/00526* (2013.01);
(Continued)

(58) Field of Classification Search
CPC .............. A61B 17/12; A61B 17/12113; A61B 17/1214; A61B 17/12145;
(Continued)

(56) References Cited

U.S. PATENT DOCUMENTS 6,165,178 A    12/2000   Bashiri et al.
2006/0271097 A1    11/2006   Ramzipoor et al.
(Continued)

FOREIGN PATENT DOCUMENTS

CN    102186426 A    9/2011
CN    107374690 A    11/2017
(Continued)

*Primary Examiner* — George J Ulsh
(74) *Attorney, Agent, or Firm* — Muncy, Geissler, Olds & Lowe, P.C.

(57) ABSTRACT

An embolic coil conveying device and a preparation method thereof are disclosed. The embolic coil conveying device includes a pusher and an embolic coil. A distal end of the pusher and a proximal end of the embolic coil are connected to serve as a detachment section. A stretch-resistant thread is disposed in the embolic coil. The stretch-resistant thread is fixed at the proximal end of the embolic coil. A conductive wire is disposed in the pusher. The stretch-resistant thread is connected to the conductive wire. Compared with the prior art, the present invention has the advantages that the stretch-resistant thread is fixed at the proximal end of the embolic coil, so that the stretch-resistant thread is connected to the conductive wire, thereby reducing the length of the detachment section, making the detachment section more flexible, and avoiding kick-out of a microcatheter due to release of the embolic coil.

13 Claims, 4 Drawing Sheets

(52) U.S. Cl.
CPC ............... *A61B 2017/1205* (2013.01); *A61B 2017/12095* (2013.01)

(58) Field of Classification Search
CPC .... A61B 17/12154; A61B 2017/00526; A61B 2017/00831; A61B 2017/00929; A61B 2017/1205; A61B 2017/12063; A61B 2017/12095
See application file for complete search history.

(56) References Cited

U.S. PATENT DOCUMENTS

2010/0094395 A1    4/2010   Kellett
2015/0182227 A1    7/2015   Le et al.

FOREIGN PATENT DOCUMENTS

| EP | 2668914 A1 | 12/2013 |
|----|------------|---------|
| JP | 2012071151 A | 4/2012 |

EMBOLISM COIL CONVEYING DEVICE AND PREPARATION METHOD THEREFOR

TECHNICAL FIELD

The present invention relates to the field of medical devices, and in particular, to an embolic coil conveying device and a preparation method thereof.

BACKGROUND

The development of intravascular interventional therapy provides new technology for the treatment of intracranial aneurysms, especially since the advent of embolic coils which has greatly improved the safety and efficacy of intravascular therapy for intracranial aneurysms, and has reached or exceeded that of craniotomy. The embolic coil is generally detached in the cavity of the cerebral aneurysm to result in blood clots in the cavity to achieve the purpose of embolization of the arterial aneurysm.

The embolic coils currently used mainly include mechanical detachable coils, thermolytic detachable coils, and electrolytic detachable coils. The most commonly used are electrolytic detachable coils, mainly including the GDCs (Guglielmi detachable coils) and Target coils from Boston Scientific. In 1991, Guglielmi, et al., first reported the use of GDC electrolytic detachable coil embolization to treat intracranial aneurysms. The distal end of the GDC is a platinum coil, which is connected to a stainless steel guide wire. The design of the embolic coil material enables the coil to reach the aneurysmal lesions of the tortuous and complicated cerebral artery. Embolization of the aneurysmal cavity with the GDC electrolytic detachable coil is achieved by carrying out percutaneous vascular puncture, introducing the coil into the arterial aneurysm by means of a microcatheter, fusing by electrolysis the part where the embolic coil is connected to the stainless steel guide wire, and detaching the embolic coil inside the arterial aneurysm, thereby preventing blood flowing into the arterial aneurysm.

A more critical step in treating intracranial aneurysms with embolic coils is that: the microcatheter is accurately put in place and can be kept at the neck of the aneurysmal cavity, the terminal end of the microcatheter is kept in the aneurysmal cavity ⅓ to ½ away from the aneurysmal neck, or at the aneurysmal neck in smaller arterial aneurysms. In this way, the resistance is small, and it is conducive to the winding of the embolic coil. At present, the significant problem of the GDC and Target coils produced by Boston Scientific, the Axium coils produced by Medtronic (Ev3), and the MicroPlex and HydroCoil coils produced by Microvention is that: the detachment section between the coil and the pusher (the detachment section refers to a section where the embolic coil and the pusher are connected, and the detachment point that is disconnected by means of electrolysis is located in this section. However, the detachment section is not equal to the detachment point, but refers to a section starting from the point of sudden softness change at the distal end of the pusher to the point of sudden softness change at the proximal end of the coil) is relatively long (at least greater than 1.5 mm, some even up to 3 mm), and stiff (the bending modulus of elasticity is at least greater than 300 Mpa). For example, an anchoring spring and Polyethylene Terephthalate (PET) tube are disposed between a coil and a pusher of the GDC coil, and the length of the detachment section is 1.6 mm. A heating spring, a support spring, PET tube and a conductive wire of the MicroPlex coil make the length of the detachment section 3.0 mm. The length of the occlusal detachment section of the PET, a hypotube and a ball of the Axium coil is 2.0 mm. These relatively long and stiff detachment sections would often cause the microcatheter kick-out effect (that is, the terminal end of the microcatheter in the aneurysmal cavity is kicked out of the aneurysmal cavity by the detached coil, and the terminal end of the microcatheter falls into the parent artery). At present, an arterial aneurysm is filled with an average of 5 to 6 coils for treatment. However, the kick-out effect causes the microcatheter to be displaced, which will inevitably require the relocation of the microcatheter in the aneurysmal cavity near the aneurysmal neck by the surgeon. In this case, the previously-filled coils block the channel, which makes it difficult for the surgeon to relocate the microcatheter, prolonging the operation time or causing surgical failure.

The inventors believe that the reason why the detachment section of the existing embolic coil is long and stiff is that the delivery guide wire is not directly connected to the embolic coil, but is connected through a functional module. An anchoring module is disposed between a delivery guide wire and a coil of the mechanical detachable coil. A heating module is disposed between a pusher and a coil of the thermolytic detachable coil. In addition, an insulating module is disposed between a delivery guide wire and a coil of the existing electrolytic detachable coil.

Therefore, how to improve the performance of the detachment section, ensure normal detachment of the embolic coil, and prevent kick-out of a microcatheter is a problem that needs to be solved.

SUMMARY OF THE INVENTION

An objective of the present invention is to provide an embolic coil conveying device and a preparation method thereof, which overcome the problem in the prior art of the kick-out of a microcatheter.

In order to solve the foregoing technical problem, the present invention provides an embolic coil conveying device, including a pusher and an embolic coil, wherein a section where a distal end of the pusher and a proximal end of the embolic coil are connected is a detachment section. The embolic coil conveying device further includes: a stretch-resistant thread disposed in the embolic coil, the stretch-resistant thread being fixed on a ring at the proximal end of the embolic coil; and a conductive wire configured to pass through an inside of the pusher. The conductive wire is covered by an insulating layer, a detachment point that is not covered by the insulating layer is provided on a distal end of the conductive wire, and the distal end of the conductive wire and the proximal end of the stretch-resistant thread are in cross connection.

Optionally, regarding the embolic coil conveying device, the stretch-resistant thread is fixed onto any one of the second to sixth rings at the proximal end of the embolic coil.

Optionally, regarding the embolic coil conveying device, the bending modulus of elasticity of the detachment section is 150-220 Mpa.

Optionally, regarding the embolic coil conveying device, the length of the detachment section is 0.3-1.0 mm.

Optionally, regarding the embolic coil conveying device, the distal end of the conductive wire is "J"-shaped, "U"-shaped, or "T"-shaped. The proximal end of the stretch-resistant thread is "J"-shaped or "U"-shaped. The conductive wire and the stretch-resistant thread are in UU-shaped cross connection, UJ-shaped cross connection, JU-shaped cross connection, JJ-shaped cross connection, TU-shaped cross connection, or TJ-shaped cross connection.

Optionally, regarding the embolic coil conveying device, a section where the conductive wire and the stretch-resistant thread are in cross connection is coated with a polymer adhesive.

Optionally, regarding the embolic coil conveying device, the material of the insulating layer includes at least one of polytetrafluoroethylene, polyethylene terephthalate, polyetheramide, and polyimide.

Optionally, the embolic coil conveying device further includes a detachment device, wherein a proximal end of the pusher is inserted into the detachment device, and the detachment device is configured to apply a direct current of 0.5 mA-5.0 mA to the conductive wire.

Optionally, regarding the embolic coil conveying device, the embolic coil is in an "Ω" basket-like shape or a helical shape.

The present invention further provides a preparation method of the embolic coil conveying device as described above, including:

providing a pusher and an embolic coil;

disposing a stretch-resistant thread in the embolic coil, and fixing the stretch-resistant thread at a proximal end of the embolic coil;

passing a conductive wire through the center of the pusher, covering the conductive wire by an insulating layer, and providing a detachment point that is not covered by the insulating layer at a distal end of the conductive wire; and cross-connecting the proximal end of the stretch-resistant thread to the distal end of the conductive wire.

Optionally, regarding the preparation method of the embolic coil conveying device, the stretch-resistant thread is fixed onto any one of the second to sixth rings at the proximal end of the embolic coil.

Optionally, regarding the preparation method of the embolic coil conveying device, the distal end of the conductive wire is "J"-shaped, "U"-shaped, or "T"-shaped. The proximal end of the stretch-resistant thread is "J"-shaped or "U"-shaped. The conductive wire and the stretch-resistant thread are in UU-shaped cross connection, UJ-shaped cross connection, JU-shaped cross connection, JJ-shaped cross connection, TU-shaped cross connection, or TJ-shaped cross connection.

Optionally, the preparation method of the embolic coil conveying device further includes: coating the cross-connection with a polymer adhesive.

In the embolic coil conveying device and the preparation method thereof provided by the present invention, the embolic coil conveying device includes: a pusher and an embolic coil. A distal end of the pusher and a proximal end of the embolic coil are connected to serve as a detachment section. A stretch-resistant thread is disposed in the embolic coil. The stretch-resistant thread is fixed at the proximal end of the embolic coil. A conductive wire is disposed in the pusher. The stretch-resistant thread is connected to the conductive wire. As opposed to the prior art, the present invention fixes the stretch-resistant thread onto a ring at the proximal end of the embolic coil, covers the conductive wire with an insulating layer, and provides a detachment point that is not covered by the insulating layer on a distal end of the conductive wire. The stretch-resistant thread and the conductive wire are in cross connection, so that the conductive wire and the stretch-resistant thread are wound and fixed onto the ring at the proximal end of the embolic coil. Such a structure reduces the length of the detachment section, and makes the detachment section more flexible, which basically avoids the kick-out of a microcatheter due to the release of the embolic coil, and improves the success rate of the operation.

DETAILED DESCRIPTION

The embolic coil conveying device and the preparation method thereof of the present invention are described in detail below with reference to the schematic diagrams, in which the preferred embodiments of the present invention are shown. It should be understood that those skilled in the art can modify the present invention described herein, while still achieving the advantageous effects of the present invention. Therefore, the following description should be understood to be widely known to those skilled in the art, but not to limit the present invention.

The present invention is described in more detail by way of example in the following paragraphs with reference to the drawings. Advantages and features of the present invention will be apparent from the description and appended claims below. It should be noted that the drawings are in a very simplified form and use non-precise proportions, and are only intended to conveniently and clearly assist in describing the objectives of embodiments of the present invention.

The present invention provides an embolic coil conveying device, including: a pusher; an embolic coil; an stretch-resistant thread disposed in the embolic coil, the stretch-resistant thread being fixed on a ring at the proximal end of the embolic coil; and a conductive wire configured to pass through an inside of the pusher. The conductive wire is covered by an insulating layer, a detachment point that is not covered by the insulating layer is provided on a distal end of the conductive wire, and the stretch-resistant thread and the conductive wire are in cross connection. Such a structural design omits an intermediate module between the conductive wire and the embolic coil, which reduces the length of the detachment section and makes the detachment section more flexible, thereby basically avoiding kick-out of a microcatheter due to the release of the embolic coil, and improving the success rate of the operation.

The preferred embodiments of the embolic coil conveying device are listed below to clearly illustrate the content of the present invention. It should be understood that the content of the present invention is not limited to the following embodiments. Other improvements made through the conventional technical measures of those skilled in the art are also within the scope of the present invention.

Figure 1:
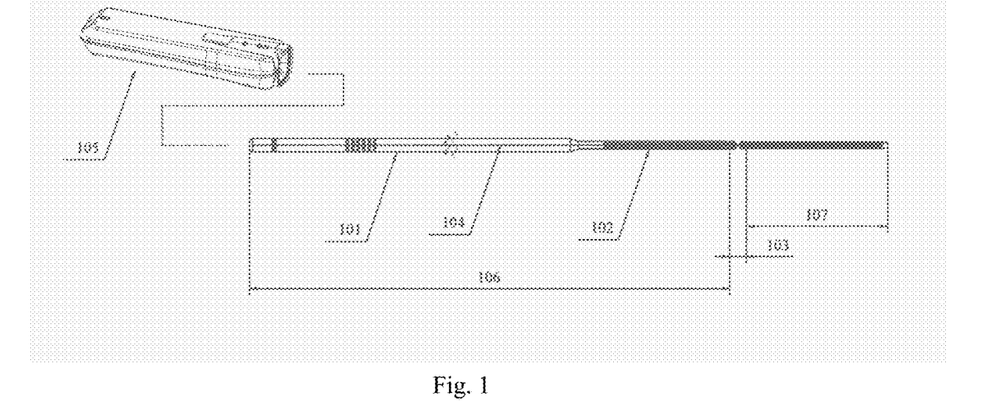
FIG. 1 is a schematic structural diagram of an embolic coil conveying device according to the present invention.

Referring to FIG. 1, the embolic coil conveying device of the present invention includes a pusher 106 and an embolic coil 107, and a section where a distal end of the pusher 106 and a proximal end of the embolic coil 107 are connected is a detachment section 103. The so-called detachment section refers to a section starting from the point of sudden softness change at the distal end of the pusher to the point of sudden softness change at the proximal end of the embolic coil and located at the point where the pusher and the embolic coil are connected, and a detachment point that is disconnected through electrolysis is located in this section. A stretch-resistant thread is provided inside the embolic coil. The stretch-resistant thread is fixed at the proximal end of the embolic coil 107. A conductive wire 104 passes through the center of the pusher 106, and the conductive wire 104 is covered by an insulating layer. The material of the insulating layer is at least one of Polytetrafluoroethylene (PTFE), Polyethylene Terephthalate (PET), Polyetheramide (PE-BAX), and polyimide. The stretch-resistant thread and the conductive wire 104 are in cross connection.

It should be noted that a "distal end" and a "proximal end" are relative concepts of the respective ends of each component or module. For example, the end close to the operator is defined as the "proximal end", and the end away from the operator is defined as the "distal end", which is common knowledge in the art and is not explained here in detail.

Figure 2:
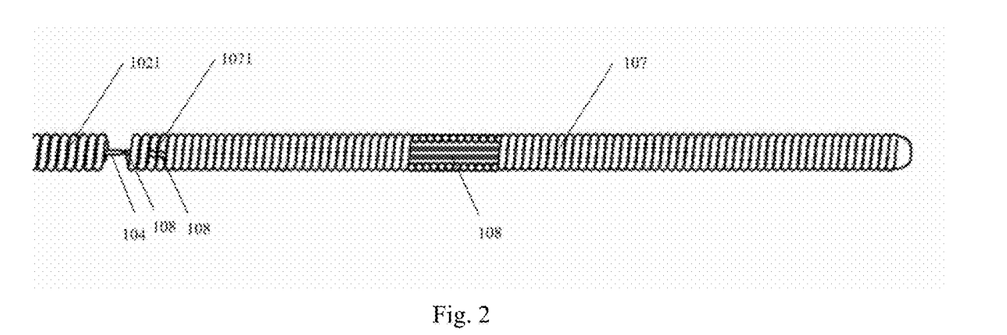
FIG. 2 is a schematic structural diagram of a detachment section and an embolic coil in FIG. 1.

Specifically, referring to FIG. 2, the stretch-resistant thread 108 is fixed onto any one of the second to sixth rings at the proximal end 1071 of the embolic coil.

In view of the above, in the present invention, the stretch-resistant thread 108 and the conductive wire 104 are connected, without using an intermediate adapter module. Moreover, the stretch-resistant thread 108 is fixed on the embolic coil 107, which can also achieve steadiness without falling off. In this way, the flexibility of the detachment section can be ensured, and the length of the detachment section can be reduced as much as possible. The terminal end of the microcatheter in the aneurysmal cavity can effectively be prevented from being kicked out of the aneurysmal cavity by the embolic coil 107 that has been released. In one embodiment, the length of the detachment section 103 is 0.3 mm to 1.0 mm.

In the present invention, the distal end of the conductive wire 104 and the proximal end of the stretch-resistant thread 108 are in cross connection. Referring to FIGS. 3-7, various optional solutions are shown.

For example, the distal end of the conductive wire 104 is "J"-shaped, "U"-shaped, or "T"-shaped. The proximal end of the stretch-resistant thread 108 is "J"-shaped or "U"-shaped.

Figure 3:
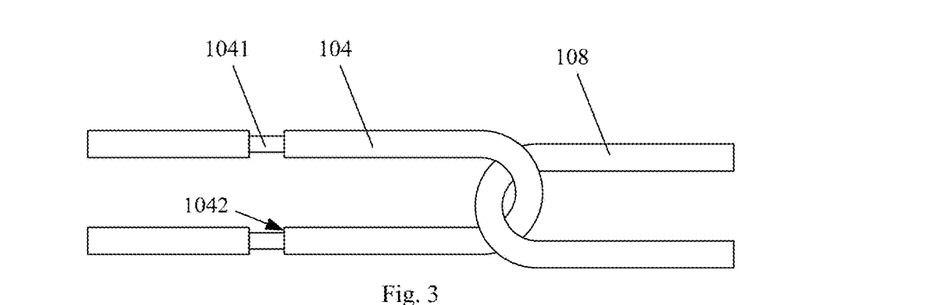
FIG. 3 is a schematic diagram of the connection between a stretch-resistant thread and a conductive wire according to an embodiment of the present invention.

As shown in FIG. 3, the distal end of the conductive wire 104 is "U"-shaped, and the proximal end of the stretch-resistant thread 108 is "U"-shaped, so that the conductive wire 104 and the stretch-resistant thread 108 are in UU-shaped cross connection.

Figure 4:
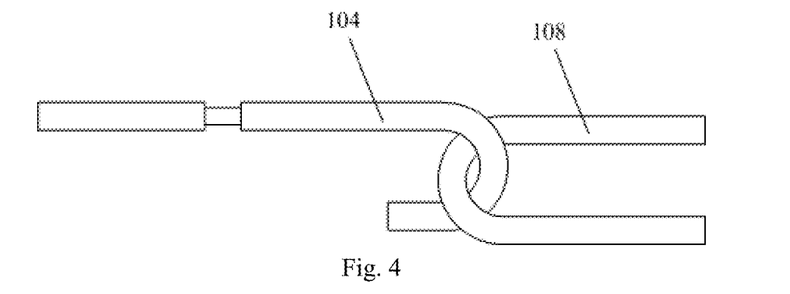
FIG. 4 is a schematic diagram of the connection between a stretch-resistant thread and a conductive wire according to an embodiment of the present invention.

As shown in FIG. 4, the distal end of the conductive wire 104 is "J"-shaped, and the proximal end of the stretch-resistant thread 108 is "U"-shaped, so that the conductive wire 104 and the stretch-resistant thread 108 are in UJ-shaped cross connection.

Figure 5:
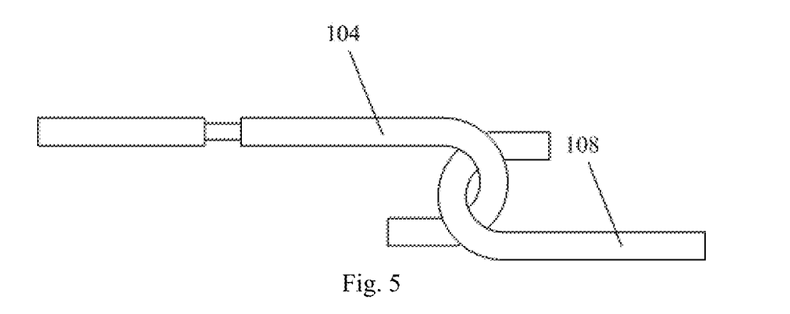
FIG. 5 is a schematic diagram of the connection between a stretch-resistant thread and a conductive wire according to an embodiment of the present invention.

As shown in FIG. 5, the distal end of the conductive wire 104 is "J"-shaped, and the proximal end of the stretch-resistant thread 108 is "J"-shaped, so that the conductive wire 104 and the stretch-resistant thread 108 are in JJ-shaped cross connection.

Figure 6:
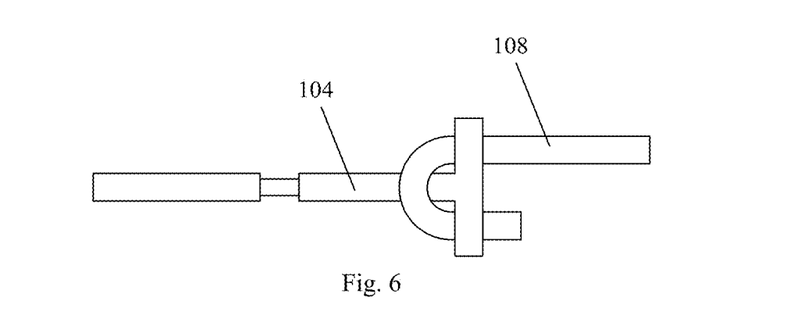
FIG. 6 is a schematic diagram of the connection between a stretch-resistant thread and a conductive wire according to an embodiment of the present invention.

As shown in FIG. 6, the distal end of the conductive wire 104 is "T"-shaped, and the proximal end of the stretch-resistant thread 108 is "J"-shaped, so that the conductive wire 104 and the stretch-resistant thread 108 are in TJ-shaped cross connection.

Figure 7:
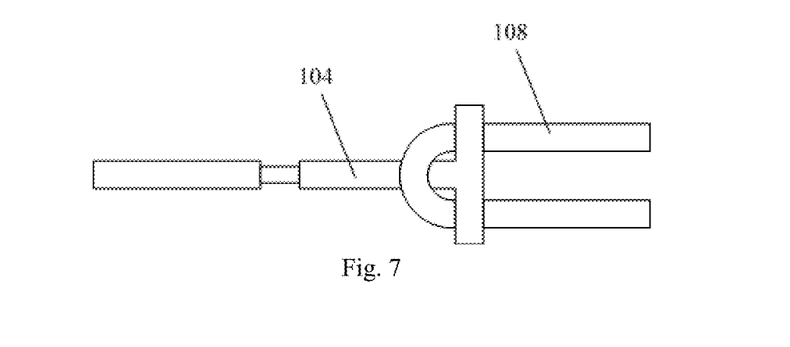
FIG. 7 is a schematic diagram of the connection between a stretch-resistant thread and a conductive wire according to an embodiment of the present invention.

As shown in FIG. 7, the distal end of the conductive wire 104 is "T"-shaped, and the proximal end of the stretch-resistant thread 108 is "U"-shaped, so that the conductive wire 104 and the stretch-resistant thread 108 are in TU-shaped cross connection.

By means of the cross connection between the distal end of the conductive wire 104 and the proximal end of the stretch-resistant thread 108, the embolic coil 107 and the pusher 106 can maintain certain connection strength, and meanwhile, the force is effectively transmitted to the embolic coil 107 to ensure the delivery of the embolic coil 107.

Certainly, the connection between the conductive wire 104 and the stretch-resistant thread 108 is not limited to the forms listed in the present invention, and those skilled in the art can flexibly choose other feasible ways.

In one embodiment, a section where the stretch-resistant thread 108 and the conductive wire 104 are connected is coated with a polymer adhesive to enhance the connection strength. For example, the polymer adhesive may be a UV adhesive, an epoxy adhesive, or the like.

Taking FIG. 3 as an example, in the present invention, the conductive wire 104 includes a coating section 1042 (i.e., an insulating layer) and an exposed section 1041. The exposed section 1041 is a narrow section at the distal end of the conductive wire 104, and is disconnected in the body fluid by means of electrolysis, so that the pusher 106 is separated from the embolic coil 107, and thus it is also called a detachment point.

The coating material of the coating section 1042 includes at least one of PTFE, PET, PEBAX, and polyimide.

In one embodiment, the material of the conductive wire 104 is a metal, for example, a metal with good biopotency, such as stainless steel, gold, silver, and iron.

Still referring to FIG. 1, the embolic coil conveying device further includes a detachment device 105. A proximal end of the pusher 106 is inserted into the detachment device 105, and the detachment device 105 applies a direct current of 0.5 mA-5.0 mA to the conductive wire 104, more specifically, for example, a current of 1.0 mA-3.0 mA, so that the embolic coil 107 and the pusher 106 can be separated safely and quickly. The detachment device 105 may be hand-held to facilitate operation.

Still referring to FIG. 1, the pusher 106 includes a metal tube 101 and a metal spring tube 102 connected to each other. The metal spring tube 102 has a length of 40-50 cm, and can smoothly pass through the tortuous intracranial vessels above the aortic arch. Accordingly, the distal end 1021 of the metal spring tube 102 is the distal end of the pusher 106, and the proximal end of the metal tube 101 can be inserted into the detachment device 105.

The embolic coil 107 is in an approximately straight state when passing through an introduction sheath and a matching microcatheter (not shown), and the embolic coil 107 is conveyed to the lesion site by means of the pusher 106. After entering the lesion site through the microcatheter, the embolic coil 107 restores its secondary form and conforms to the shape of the lesion site. The embolic coil 107 can be detached from the distal end of the pusher to complete the implantation by means of the detachment device 105 outside of the body.

Figure 8:
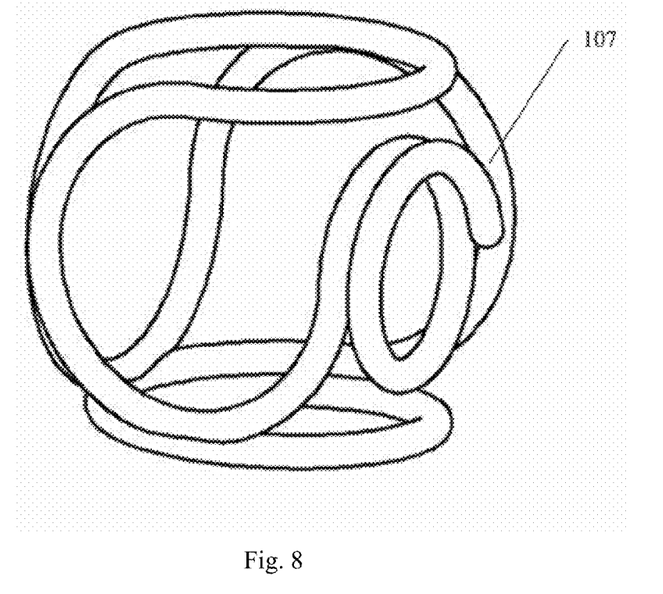
FIG. 8 is a schematic diagram of an embolic coil according to an embodiment of the present invention.
Figure 9:
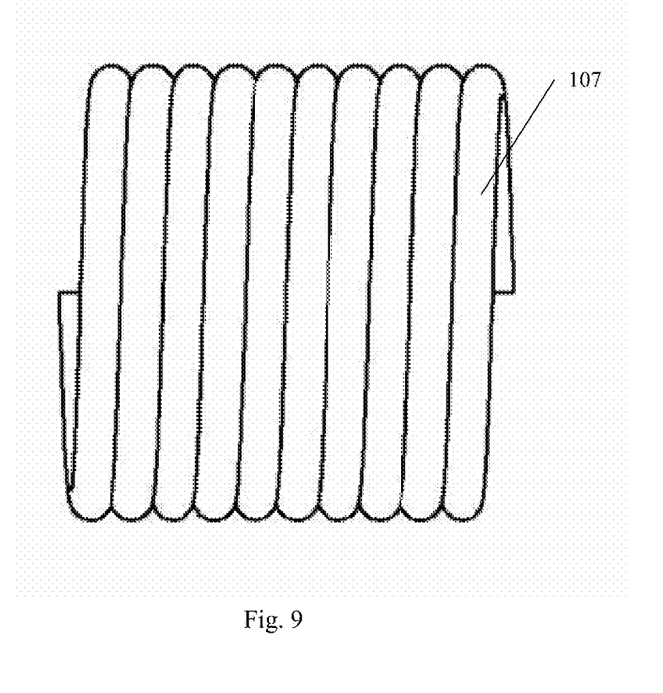
FIG. 9 is a schematic diagram of an embolic coil according to an embodiment of the present invention.

Referring to FIGS. 8 and 9, the secondary form of the embolic coil 107 is in an "Ω" basket-like shape or a helical shape. Certainly, according to different needs, embolic coils 107 of other shapes may be provided to adapt to aneurysms of different sizes.

The present invention further provides a preparation method of an embolic coil conveying device, including:

providing a pusher and an embolic coil;

disposing a stretch-resistant thread in the embolic coil, and fixing the stretch-resistant thread onto a ring at a proximal end of the embolic coil;

disposing a conductive wire in the pusher, and providing an insulating layer on the conductive wire and a detachment point that is not covered by the insulating layer at the distal end of the conductive wire; and connecting the stretch-resistant thread to the conductive wire, so that the distal end of the pusher and the proximal end of the embolic coil are connected to serve as a detachment section.

In one embodiment, the stretch-resistant thread is fixed onto any one of the second to sixth rings of the embolic coil.

In one embodiment, after connecting the stretch-resistant thread to the conductive wire, the method further includes: coating a section where the stretch-resistant thread and the conductive wire are connected with a polymer adhesive to enhance the connection strength.

The embolic coil can be wound with platinum alloy wires, and the platinum alloy coils can have various lengths and diameters. For example, a platinum alloy wire can be wound around a mandrel to form a primary coil, and then the wound primary coil can further be wound on a mold according to a preset shape and subject to a shaping process, for example, to obtain a structure with the secondary form of an "Ω" basket-like shape or a helical shape.

In one embodiment, the platinum alloy coil is made of a wire with a diameter of 0.003 inch, and is wound on a metal mandrel to form compact primary coils. These primary coils are used as the embolic coil 107. The wound primary coil is wound according to a preset secondary form of an "Ω" basket-like shape and subject to a shaping process, that is, the obtained secondary form of the embolic coil 107 is in an "Ω" basket-like shape.

The distal end of the conductive wire 104 is made into a "U" shape (as shown in FIG. 3). The stretch-resistant thread 108 is axially extended inside the embolic coil 107 along the primary coil (as shown in a partial cross-sectional view in FIG. 2), and the stretch-resistant thread 108 is in cross connection with the "U"-shaped distal end of the conductive wire 104 to form a U-shaped proximal end (as shown in FIG. 3). One side of the "U"-shape of the proximal end of the stretch-resistant thread 108 is fixedly wound around any one of the second to sixth rings of the proximal end of the embolic coil 107 (as shown in FIG. 2), and the other side returns to the distal end of the embolic coil 107, and optionally, a ball cap is formed at the distal end of the embolic coil 107 for fixation. An insulating layer 1042 is disposed on the conductive wire 104, and a detachment point 1041 (as shown in FIG. 3) that is not covered by the insulating layer is provided on the distal end of the conductive wire 104. A detachment section 103 is formed in a section where the conductive wire 104 and the stretch-resistant thread 108 are in cross connection. The length of the detachment section 103 is 0.5 mm. According to the three-point bending method shown in FIG. 10, the bending modulus of elasticity of the detachment section 103 is 150 Mpa.

Figure 10:
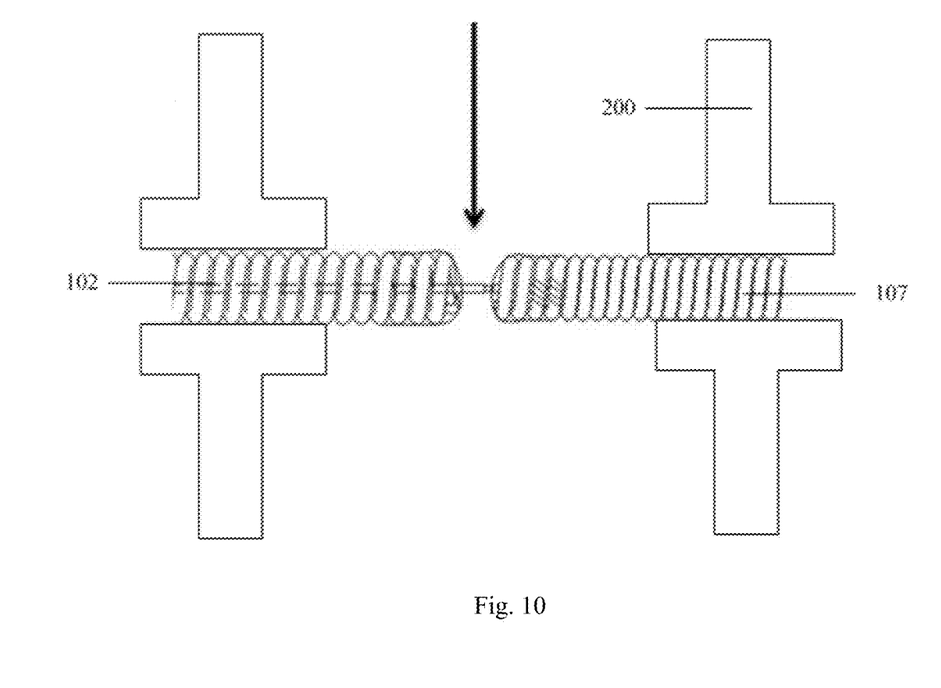
FIG. 10 is a schematic diagram of the measurement of a bending modulus of elasticity of a detachment section according to an embodiment of the present invention.

The three-point bending method shown in FIG. 10 includes: clamping the metal spring tube 102 and the embolic coil 107 respectively by a fixing device 200 after the conductive wire 104 and the stretch-resistant thread 108 are in cross connection to form the detachment section 103, and then applying a certain force to the detachment section 103, for example, pressing down by 10 mm, so as to calculate the bending modulus of elasticity.

In one embodiment, the embolic coil 107 has a helical structure (as shown in FIG. 9). The platinum alloy coil is made of a wire with a diameter of 0.00125 inch, and is similarly wound on the metal mandrel to form compact primary coils. The wound primary coils are subject to a shaping process according to a preset "helical" shape.

The distal end of the conductive wire 104 is made into a "J" shape (as shown in FIG. 4). The stretch-resistant thread 108 is axially extended along the primary coil, and the stretch-resistant thread 108 is in cross connection with the "J"-shaped distal end of the conductive wire 104 to form a U-shaped proximal end (as shown in FIG. 4). One side of the "U"-shape of the proximal end of the stretch-resistant thread 108 is fixedly wound around any one of the second to the sixth rings at the proximal end of the embolic coil 107 (as shown in FIG. 2), the other side returns to the distal end of the embolic coil 107. An insulating layer is disposed on the conductive wire, and a detachment point that is not covered by the insulating layer is provided on the distal end of the conductive wire. A detachment section 103 is formed in a section where the conductive wire 104 and the stretch-resistant thread 108 are in cross connection. The length of the detachment section 103 is 1.0 mm. According to the three-point bending method shown in FIG. 10, the bending modulus of elasticity of the detachment section 103 is 210 Mpa.

In one embodiment, the embolic coil 107 has a helical structure (as shown in FIG. 9). The platinum alloy coil is made of a wire with a diameter of 0.002 inch, and is similarly wound on the metal mandrel to form compact primary coils. The wound primary coils are subject to a shaping process according to a preset "helical" shape.

The distal end of the conductive wire 104 is made into a "J" shape (as shown in FIG. 5). The stretch-resistant thread 108 is axially extended along the primary coil, and the stretch-resistant thread 108 is in cross connection with the "J"-shaped distal end of the conductive wire 104 to form a J-shaped proximal end (as shown in FIG. 5). One side of the "J"-shaped proximal end of the stretch-resistant thread 108 is fixedly wound around the third ring at the proximal end of the embolic coil 107. An insulating layer is disposed on the conductive wire, and a detachment point that is not covered by the insulating layer is provided on the distal end of the conductive wire. A detachment section 103 is formed in a section where the conductive wire 104 and the stretch-resistant thread 108 are in cross connection. The length of the detachment section 103 is 0.5 mm. According to the three-point bending method shown in FIG. 10, the bending modulus of elasticity of the detachment section 103 is 150 Mpa.

In one embodiment, the distal end of the conductive wire 104 is designed to a "T" shape (as shown in FIGS. 6 and 7). The stretch-resistant thread 108 is axially extended along the primary coil, and the proximal end of the stretch-resistant thread 108 is designed to a "J" shape (as shown in FIG. 6) or a "U" shape (as shown in FIG. 7). An insulating layer is disposed on the conductive wire, and a detachment point that is not covered by the insulating layer is provided on the distal end of the conductive wire, and the conductive wire 104 and the stretch-resistant thread 108 are in cross connection.

For the cross connection mode shown in FIGS. 4-7, preferably, a section where the stretch-resistant thread 108 and the conductive wire 104 are in cross connection is coated with a polymer adhesive to enhance the connection strength.

It can be known from the foregoing description that in the embolic coil conveying device and the preparation method provided by the present invention, the embolic coil conveying device includes a pusher and an embolic coil. A distal end of the pusher and a proximal end of the embolic coil are connected to serve as a detachment section. A stretch-resistant thread is disposed in the embolic coil. The stretch-resistant thread is fixed at the proximal end of the embolic coil. A conductive wire is disposed in the pusher. An insulating layer is disposed on the conductive wire, and a detachment point that is not covered by the insulating layer is provided at the distal end of the conductive wire. The stretch-resistant thread is connected to the conductive wire. Compared with the prior art, the present invention fixes the stretch-resistant thread at the proximal end of the embolic coil, so that the stretch-resistant thread is connected to the conductive wire, which reduces the length of the detachment section and makes the detachment section more flexible, thereby basically avoiding the kick-out of a microcatheter due to release of the embolic coil, and improving the success rate of the operation.

Various modifications and variations can be made to the present invention by those skilled in the art without departing from the spirit and scope of the present invention. In this way, if the modifications and variations made to the present invention fall within the scope of the claims and equivalent techniques thereof of the present invention, the present invention is also intended to include the modifications and variations.

What is claimed is:

1. An embolic coil conveying device, comprising a pusher and an embolic coil, wherein a section where a distal end of the pusher and a proximal end of the embolic coil are connected is a detachment section;
wherein the embolic coil conveying device further comprises: a stretch-resistant thread disposed in the embolic coil, the stretch-resistant thread being fixed on a ring at the proximal end of the embolic coil; and a conductive wire configured to pass through an inside of the pusher, wherein the conductive wire is covered by an insulating layer, and a detachment point that is not covered by the insulating layer is provided on a distal end of the conductive wire, and wherein the distal end of the conductive wire and a proximal end of the stretch-resistant thread are directly cross-connected.

2. The embolic coil conveying device according to claim 1, wherein the stretch-resistant thread is fixed on any one of a second to a sixth ring at the proximal end of the embolic coil.

3. The embolic coil conveying device according to claim 1, wherein the detachment section has a bending modulus of elasticity of 150-220 Mpa.

4. The embolic coil conveying device according to claim 1, wherein the detachment section has a length of 0.3 mm-1.0 mm.

5. The embolic coil conveying device according to claim 1, wherein the distal end of the conductive wire is "J"-shaped, "U"-shaped, or "T"-shaped; the proximal end of the stretch-resistant thread is "J"-shaped or "U"-shaped; and the conductive wire and the stretch-resistant thread are in UU-shaped cross connection, UJ-shaped cross connection, JU-shaped cross connection, JJ-shaped cross connection, TU-shaped cross connection, or TJ-shaped cross connection.

6. The embolic coil conveying device according to claim 1, wherein a section where the conductive wire and the stretch-resistant thread are in cross connection is coated with a polymer adhesive.

7. The embolic coil conveying device according to claim 1, wherein a material of the insulating layer comprises at least one of polytetrafluoroethylene, polyethylene terephthalate, polyetheramide, and polyimide.

8. The embolic coil conveying device according to claim 1, further comprising a detachment device, wherein a proximal end of the pusher is inserted into the detachment device, and the detachment device is configured to apply a direct current of 0.5-5.0 mA to the conductive wire.

9. The embolic coil conveying device according to claim 1, wherein the embolic coil is in an "Ω" basket-like shape or a helical shape.

10. A preparation method of the embolic coil conveying device according to claim 1, comprising:
providing the pusher and the embolic coil;
disposing the stretch-resistant thread in the embolic coil, and fixing the stretch-resistant thread at the proximal end of the embolic coil;
passing the conductive wire through an interior of the pusher, covering the conductive wire by the insulating layer, and providing the detachment point that is not covered by the insulating layer at the distal end of the conductive wire; and
directly cross-connecting a proximal end of the stretch-resistant thread to the distal end of the conductive wire.

11. The preparation method of the embolic coil conveying device according to claim 10, wherein the stretch-resistant thread is fixed onto any one of a second to a sixth ring at the proximal end of the embolic coil.

12. The preparation method of the embolic coil conveying device according to claim 10, wherein the distal end of the conductive wire is "J"-shaped, "U"-shaped, or "T"-shaped; the proximal end of the stretch-resistant thread is "J"-shaped or "U"-shaped; and the conductive wire and the stretch-resistant thread are in UU-shaped cross connection, UJ-shaped cross connection, JU-shaped cross connection, JJ-shaped cross connection, TU-shaped cross connection, or TJ-shaped cross connection.

13. The preparation method of the embolic coil conveying device according to claim 10, further comprising coating the cross-connection with a polymer adhesive.

* * * * *